(12) United States Patent
Kappel et al.

(10) Patent No.: US 9,511,397 B2
(45) Date of Patent: Dec. 6, 2016

(54) ROTARY OR LINEAR BEVERAGE BOTTLE CLEANING MACHINE CONFIGURED TO CLEAN BEVERAGE BOTTLES DISPOSED UPSIDE-DOWN WHICH MACHINE INCLUDES APPARATUS FOR CLEANING ROTARY OR LINEAR BEVERAGE BOTTLE CLEANING MACHINE IN A FILLING PLANT AND ROTARY OR LINEAR CONTAINER CLEANING MACHINE CONFIGURED TO CLEAN CONTAINERS WITH APPARATUS FOR CLEANING THE CONTAINER CLEANING MACHINE

(75) Inventors: Steffen Kappel, Winzenheim (DE); Klaus Baumgartner, Bad Kreuznach (DE)

(73) Assignee: KHS GmbH, Dortmund (DE)

( * ) Notice: Subject to any disclaimer, the term of this patent is extended or adjusted under 35 U.S.C. 154(b) by 1729 days.

(21) Appl. No.: 12/369,409

(22) Filed: Feb. 11, 2009

(65) Prior Publication Data
US 2010/0037925 A1    Feb. 18, 2010

Related U.S. Application Data

(63) Continuation-in-part of application No. PCT/EP2007/007188, filed on Aug. 15, 2007.

(30) Foreign Application Priority Data

Aug. 16, 2006  (DE) .................. 10 2006 038 255

(51) Int. Cl.
| | | |
|---|---|---|
| B08B 9/28 | (2006.01) | |
| B08B 9/34 | (2006.01) | |
| B05B 15/02 | (2006.01) | |
| B67C 3/00 | (2006.01) | |

(Continued)

(52) U.S. Cl.
CPC ............. B08B 9/34 (2013.01); B05B 15/0258 (2013.01); B08B 3/02 (2013.01); B08B 9/20 (2013.01);

(Continued)

(58) Field of Classification Search
CPC .......... B67C 3/001; B67C 3/002; B67C 3/004; B67C 3/005; B05B 15/0275; B05B 15/0258; B05B 15/025; B05B 15/02; B08B 3/126; B08B 9/0813; B08B 9/0826; B08B 9/34; B08B 9/20; B67D 1/07; B67D 2001/075

(Continued)

(56) References Cited

U.S. PATENT DOCUMENTS

| | | | | |
|---|---|---|---|---|
| 1,161,468 A | * | 11/1915 | Gallup ............................... 15/95 |
| 2,354,308 A | * | 7/1944 | Everett ..................... B08B 9/32 |
| | | | | 15/304 |

(Continued)

FOREIGN PATENT DOCUMENTS

| | | |
|---|---|---|
| DE | 2553989 A1 * | 8/1976 |
| DE | 3722495 A1 * | 1/1989 |

(Continued)

OTHER PUBLICATIONS

Machine translation of DE 2553989 A1, dated Aug. 1976.*

(Continued)

*Primary Examiner* — Michael Barr
*Assistant Examiner* — Kevin G Lee
(74) *Attorney, Agent, or Firm* — Nils H. Ljungman & Associates

(57) ABSTRACT

A rotary or linear beverage bottle cleaning machine configured to clean beverage bottles disposed upside-down which machine includes apparatus for cleaning rotary or linear beverage bottle cleaning machine in a filling plant and rotary (Continued)

or linear container cleaning machine configured to clean containers with apparatus for cleaning the container cleaning machine. The abstract of the disclosure is submitted herewith as required by 37 C.F.R. §1.72(b). As stated in 37 C.F.R. §1.72(b): A brief abstract of the technical disclosure in the specification must commence on a separate sheet, preferably following the claims, under the heading "Abstract of the Disclosure." The purpose of the abstract is to enable the Patent and Trademark Office and the public generally to determine quickly from a cursory inspection the nature and gist of the technical disclosure. The abstract shall not be used for interpreting the scope of the claims. Therefore, any statements made relating to the abstract are not intended to limit the claims in any manner and should not be interpreted as limiting the claims in any manner.

16 Claims, 12 Drawing Sheets

(51) Int. Cl.
  *B08B 3/02* (2006.01)
  *B08B 9/20* (2006.01)
  *B67D 1/07* (2006.01)
  *A61L 2/18* (2006.01)
  *A61L 2/22* (2006.01)
(52) U.S. Cl.
  CPC ............... *B67C 3/001* (2013.01); *B67C 3/005* (2013.01); *A61L 2/18* (2013.01); *A61L 2/22* (2013.01); *B67D 2001/075* (2013.01)
(58) Field of Classification Search
  USPC ........... 134/166 R–169 C, 182–183, 201, 43, 62,134/170; 239/24, 288–288.5, 461
  See application file for complete search history.

(56) References Cited

U.S. PATENT DOCUMENTS

| | | | | |
|---|---|---|---|---|
| 4,987,934 A * | 1/1991 | Groom | ............................ | 141/89 |
| 5,277,207 A * | 1/1994 | Perrier | ............................ | 134/44 |
| 5,409,545 A * | 4/1995 | Levey et al. | ................ | 134/22.18 |
| 6,328,928 B1 * | 12/2001 | Schroeder et al. | ............. | 422/28 |
| 8,002,900 B2 * | 8/2011 | Le Roux | .................... | 134/22.11 |
| 2003/0188769 A1 | 10/2003 | Eisenberg et al. | | |
| 2007/0144610 A1 * | 6/2007 | Berger | ............................ | 141/286 |

FOREIGN PATENT DOCUMENTS

| | | |
|---|---|---|
| DE | 44 25 219 | 1/1996 |
| DE | 198 24 991 | 12/1999 |
| DE | 299 03 939 | 3/2000 |
| EP | 1 281 446 | 2/2003 |
| JP | 08318240 A * | 12/1996 |
| JP | H08-318240 A | 12/1996 |
| JP | 09175597 A * | 7/1997 |
| JP | H10-338296 A | 12/1998 |
| JP | H1119611 | 1/1999 |
| JP | 2005-132383 A | 5/2005 |
| JP | 2005132383 A * | 5/2005 |

OTHER PUBLICATIONS

Machine translation of DE 3722495 A1, dated Jan. 1989.*
Machine translation of JP 09175597 A, dated Jul. 1997.*
Machine translation of DE 4425219 A1, dated Jan. 1996.*
International Search Report PCT/EP2007/007188 and English translation thereof.

* cited by examiner

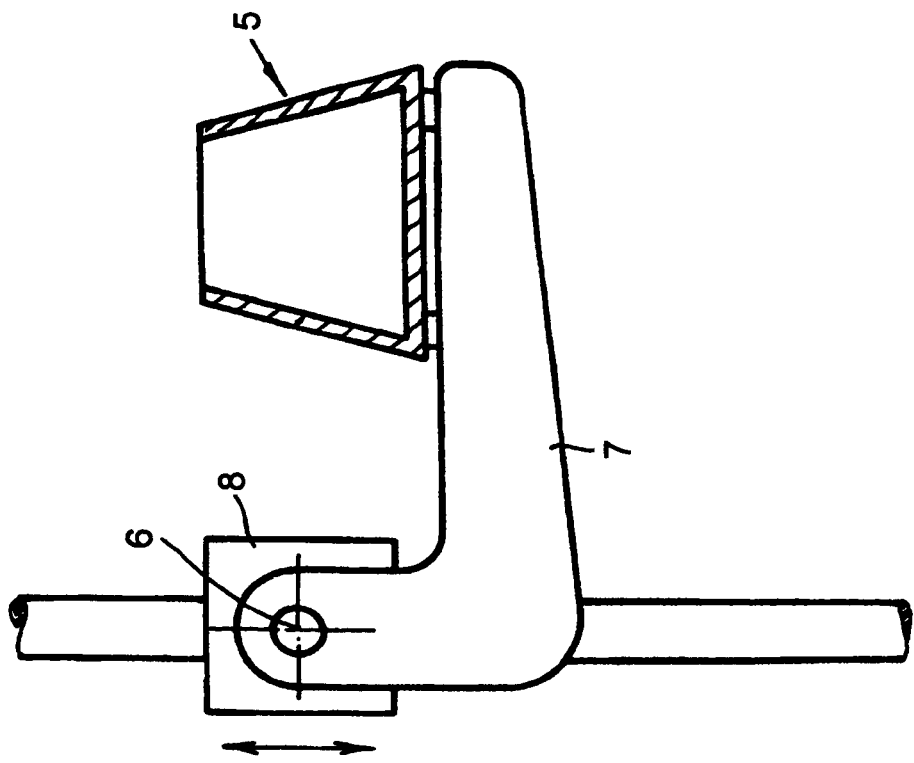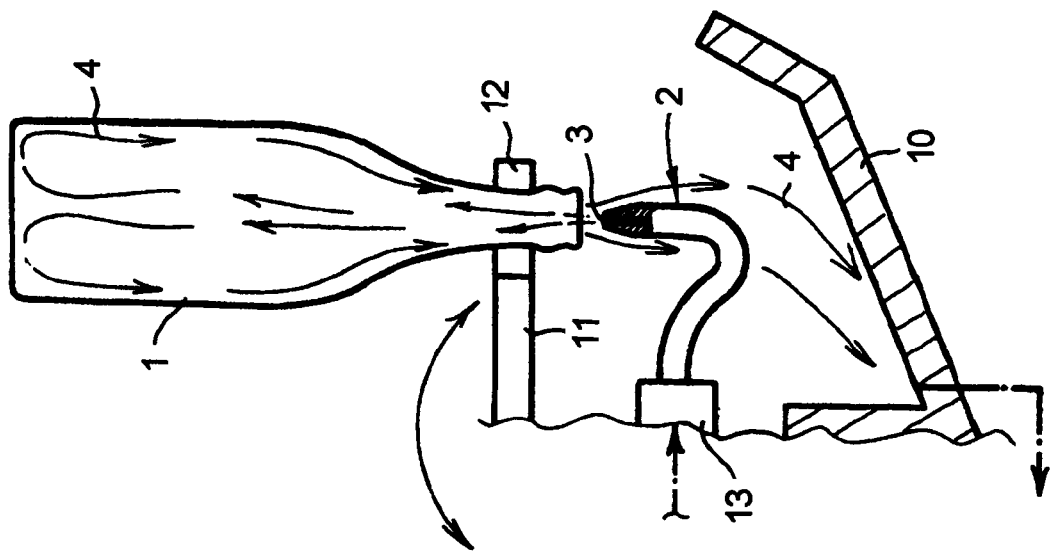
FIG. 1

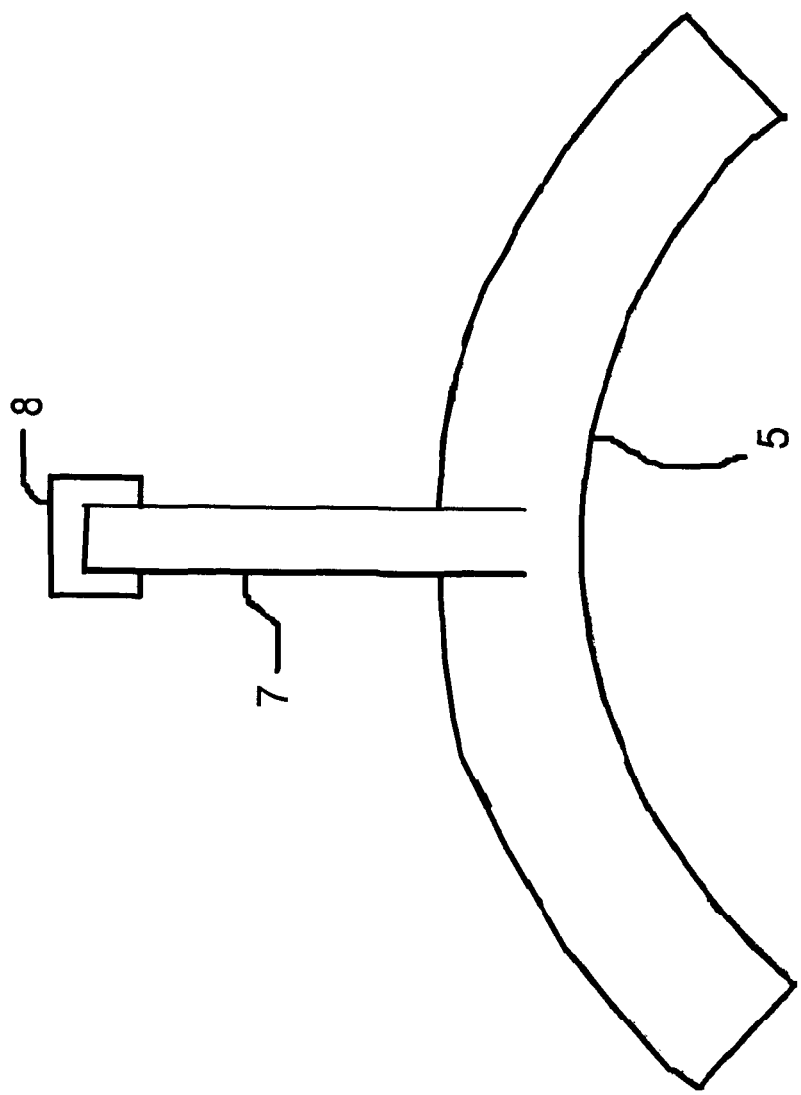

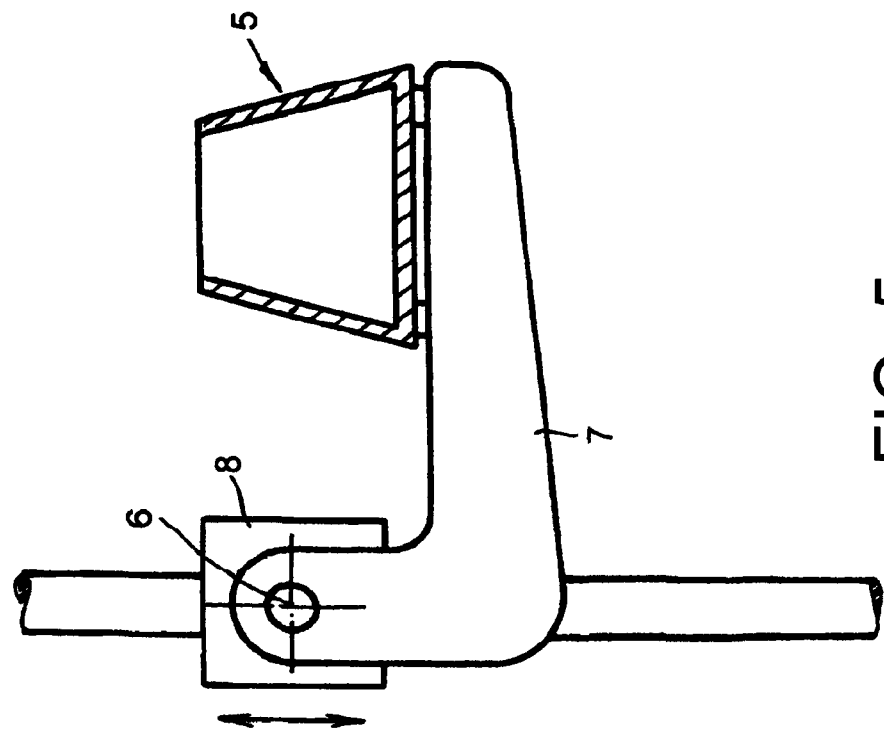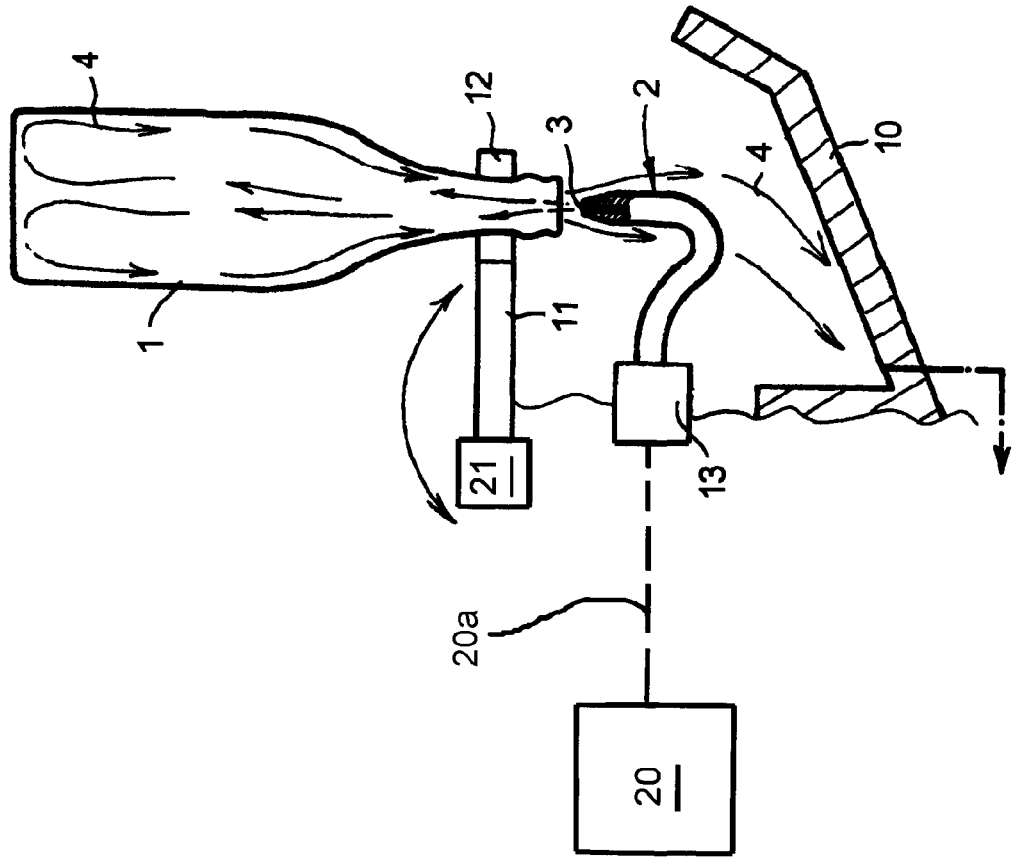
FIG. 5

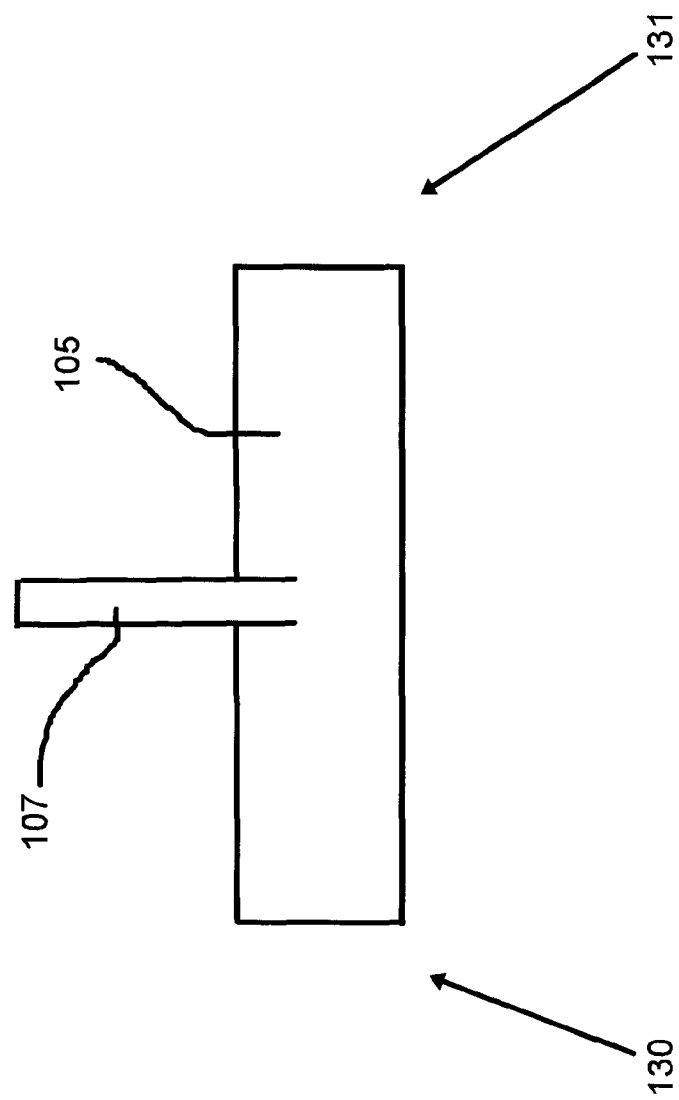

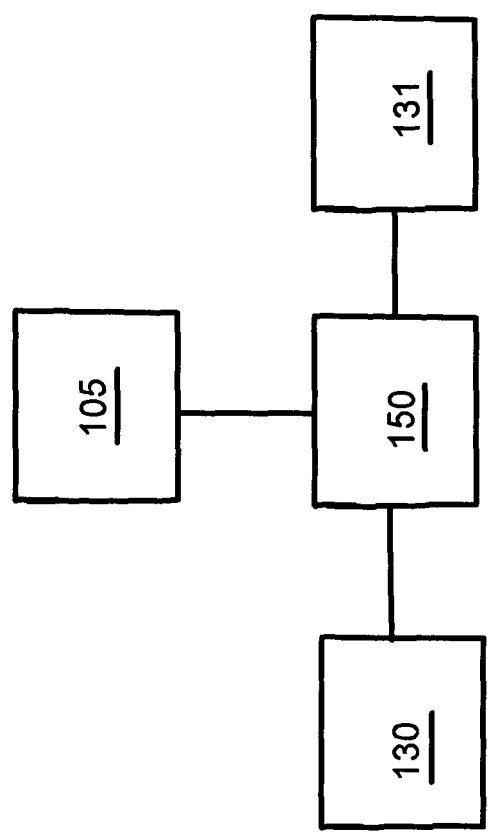

ROTARY OR LINEAR BEVERAGE BOTTLE CLEANING MACHINE CONFIGURED TO CLEAN BEVERAGE BOTTLES DISPOSED UPSIDE-DOWN WHICH MACHINE INCLUDES APPARATUS FOR CLEANING ROTARY OR LINEAR BEVERAGE BOTTLE CLEANING MACHINE IN A FILLING PLANT AND ROTARY OR LINEAR CONTAINER CLEANING MACHINE CONFIGURED TO CLEAN CONTAINERS WITH APPARATUS FOR CLEANING THE CONTAINER CLEANING MACHINE

CONTINUING APPLICATION DATA

This application is a Continuation-in-Part application of International Patent Application No. PCT/EP2007/007188, filed on Aug. 15, 2007, which claims priority from Federal Republic of Germany Patent Application No. 10 2006 038 255.2, filed on Aug. 16, 2006. International Patent Application No. PCT/EP2007/007188 was pending as of the filing date of this application. The United States was an elected state in International Patent Application No. PCT/EP2007/007188.

BACKGROUND

1. Technical Field

The present application relates to a rotary or linear beverage bottle cleaning machine configured to clean beverage bottles disposed upside-down which machine includes apparatus for cleaning rotary or linear beverage bottle cleaning machine in a filling plant and rotary or linear container cleaning machine configured to clean containers with apparatus for cleaning the container cleaning machine.

2. Background Information

Background information is for informational purposes only and does not necessarily admit that subsequently mentioned information and publications are prior art.

Some apparatuses are for the upside-down cleaning of bottles. Similar devices are widely used in existing installations.

Similar devices are known from actual practice and are for the cleaning and/or sterilization of a rinsing machine for bottles. For this purpose, a rinsing cap that is open on one side can be placed on the respective nozzle. This process can also be motorized and performed by means of a manipulator.

The cleaning of containers, and for example the cleaning of bottles before they are filled, involves removing dust, dirt, plastic particles, etc. from the bottles. For this purpose, the bottles can be placed in an upside down position and while the bottles or containers are in this upside-down position the interior of the bottles or the interior of the containers is cleaned or "rinsed," as this process is called in the technical jargon, using a rinsing fluid. The upside-down position of the bottles or containers essentially guarantees or promotes that the (gas or liquid) disinfecting/cleaning agent that is injected will subsequently be discharged from the respective container or bottles completely under the effect of gravity.

For this purpose, the disinfecting/cleaning agent in question is generally sprayed or injected into the interior of the container by means of a nozzle provided on the top of the spray tube and is likewise circulated along the bottom of the container, across the container walls and finally the mouth of the container, from which it exits the respective container or bottle. To collect the disinfecting/cleaning agent which now comprises contaminating particles or contaminated particles, for example, a collecting basin is generally provided underneath the spray tube.

An increasing number of bottling processes have recently incorporated cold-aseptic bottling. As part of this process, and for the cleaning of the container handling or filling equipment, a disinfecting/cleaning agent is used which not only removes the above mentioned miscellaneous particles or dirt from the surfaces of the container treatment machines, but also kills any germs that may be present under some circumstances. This process is generally conducted at relatively low temperatures (room temperature), although the present application naturally also includes treatment with live steam, for example.

During the cleaning of the plant, in order to wet the equipment no more than absolutely necessary or desired with the used, not altogether hygienically acceptable cleaning agent, a cover device is now also provided as a replacement for the bottle or container. In other words, the cover device is used alternatively as a replacement for a bottle or a container during the equipment cleaning. The spray tube is operated as usual, and dispenses the disinfecting/cleaning agent used for the cleaning of the plant, although under these conditions the disinfecting/cleaning agent does not get into the interior of the containers, but strikes the cover device, and from there it also strikes the spray tube, its nozzle and any optional support and pivoting devices for the container or the bottle. Consequently, these parts of the plant are cleaned or disinfected, whereby in turn the disinfecting/cleaning agent that may be contaminated with the potential dirt particles and/or germs is collected from the collecting basin which is located underneath. The feed or drain lines of the rinsing medium are simultaneously or substantially simultaneously cleaned or disinfected by this process.

To transfer the cover apparatus from its idle position into an operating position in which it functions as a container replacement, for example for the circulation of the disinfecting/cleaning agent in the course of cleaning the equipment, a manual pivoting process is initiated. This pivoting process has the basic problem that any manual intervention (either repeated or for the first time) can introduce germs into the system or cleaning system. The cleaning routine by means of the cover apparatus, is thereby negated or at least adversely affected, for example in systems for cold-aseptic bottling, where a time-consuming cleaning procedure is required and/or desired on account of this manual intervention. This is one of the disadvantages eliminated, restricted, and/or minimized by the present application.

OBJECT OR OBJECTS

An object of the present application is to develop an apparatus for the treatment of containers of the type described above so that the cleaning action is improved, and in one possible embodiment can be done in a sterile manner, and once a sterile condition is achieved, it can be maintained for a longer period because it eliminates, restricts, and/or minimizes manual interventions.

Another object of the present application is to develop an apparatus for the treatment of containers, for example for the upside-down cleaning of bottles, with a spray tube to spray the interior of the container with a disinfecting/cleaning agent and with a cover apparatus as a container replacement for the possible circulation of the disinfecting/cleaning agent during a plant cleaning.

SUMMARY

The present application relates to an apparatus for the treatment of containers, for example for the upside-down cleaning of bottles, with a spray tube for the treatment of the interior of the container with a disinfecting/cleaning agent, and with a cover apparatus in the form of a container replacement for the circulating transport of the disinfecting/cleaning agent in the process of a plant cleaning.

To accomplish at least one of these object, the present application teaches an apparatus for the treatment of containers, in one possible embodiment for the upside-down cleaning of bottles, wherein the cover apparatus can be pivoted by a motor from an idle position into an operating position and back again.

To accomplish this object, the present application is based on a generic apparatus for the treatment of containers, in one possible embodiment for the upside-down cleaning of bottles, wherein the cover apparatus is connected to a lever that can be pivoted around an axis of rotation and can be pivoted by means of a motor from an idle position into an operating position and back, and that the cover apparatus is realized so that its height can be varied in relation to the spray tube and is also connected to an actuator.

At least one object of the present application is accomplished by developing an apparatus of this type so that the cleaning action is improved and in one possible embodiment so that a high degree of sterility is achieved.

The apparatus according to the present application to accomplish at least one object is configured in at least one possible embodiment so that the cover apparatus is connected to a lever that can pivot around an axis of rotation and can be pivoted by a motor from an idle position into an operating position and back, and that the cover apparatus is vertically adjustable with reference to the spray tube and is also connected to an actuator.

In other words, the present application teaches that the cover apparatus is no longer transferred manually, but by means of a motor, from its idle position into the operating position and back again. In this manner the human being is eliminated as a potential (additional) source of germs in the treatment of the containers and in one possible embodiment in the upside-down cleaning of bottles in the field of cold-aseptic bottling. That is because the change from the idle position to the operating position can be initiated from a location that is at a distance from the apparatus, e.g. by actuating one or more drive motors. In fact, the cover apparatus is conventionally connected to a lever which can pivot around an axis of rotation, and the lever in question can be a one-armed lever. In this case, the axis of rotation is on the end of the one-armed lever. Of course, constructions with two-armed levers are also conceivable, in which case the cover device is located on one end and a counterweight is located on the other end.

In each case, the drive motor is engaged on the axis of rotation for the pivotable lever or itself defines the axis of rotation. The drive motor is thereby generally realized in the form of a rotation motor. In the first case, the drive motor may be engaged with the axis of rotation via transmission means and take care of the pivoting of the lever. In the latter variant, the pivotable lever can be installed directly on an output shaft of the drive motor, which thereby defines the axis of rotation.

At least one possible embodiment according to the present application, the cover apparatus is realized in the form of a nozzle which is at a variable distance from the head-end of the spray tube or the height of which is variable. It thereby becomes possible to take into consideration the disinfection/cleaning agent used and its pressure and/or flow velocity as the agent exits the nozzle. For example, if the exit velocity of the disinfection/cleaning agent is high and there is a sharply focused beam, the operation will be conducted at a relatively large distance from the cover apparatus, to prevent, restrict and/or minimize spraying the disinfection/cleaning agent all over or substantially all over during the equipment cleaning, or at least keeping the area sprayed as small as possible. In other cases, the cleaning can be performed at a closer distance.

Other measures with the same objective can be considered, in which case the cover apparatus has an overall curved shape, and is also realized with at least one curved leg pointing toward the collecting basin. In fact, this at least one curved leg essentially ensures or promotes that the disinfecting/cleaning agent is directed in a targeted manner from the cover apparatus to the optional pivoting device for the container, a retaining ring, the nozzle of the spray tube, the spray tube and optionally other parts of the plant, which in this manner are given the desired cleaning/disinfection.

In one possible embodiment according to the present application, the cover apparatus, viewed in cross section, is essentially in the shape of an inverted U, with a base and at least two lateral boundary legs. Generally, the disinfecting/cleaning agent that is discharged from the nozzle of the spray tube hits the base and is guided along the lateral boundary legs. In one possible embodiment, the cover apparatus can be realized so that when viewed in cross section, it has a closed configuration, except for an introductory opening for the nozzle of the spray tube. The cover apparatus is also generally provided with a return line for the disinfecting/cleaning agent, so that the overall result is a closed circuit circulation of the disinfecting/cleaning agent, although this latter feature is of course not a requirement and may not be desired.

The result is an apparatus for the treatment of containers, in one possible embodiment for the upside-down cleaning of bottles, which comprises often a high degree of sterility. Basically, this sterility is achieved because all or substantially all or most of the cleaning sequences are performed and initiated mechanically, without the need or desire for any human intervention. An operator is required only and/or desired if and when, for example, damaged containers disrupt operations. All or substantially all or most of the cleaning processes, on the other hand, are performed with practically no human intervention or minimal human intervention and mechanically, and are therefore practically sterile or as sterile as possible.

In at least one possible embodiment according to the present application, the medium used to sterilize or clean the machine and equipment is different than the medium used to sterilize or clean the beverage bottles or containers. For example, a first cleaning medium flows through the spray tubes and out of the nozzles into the containers, which are disposed upside-down and above the nozzles. Once the machine is emptied of cleaned bottles or bottles to be cleaned and the cover apparatuses are moved into the working position above the nozzles, the first cleaning medium is stopped from flowing through the spray tubes and out of the nozzles. A second cleaning medium is then ejected from the nozzles and is deflected by the cover apparatus.

In one possible embodiment of the present application, the spray tubes could be connected to a reservoir, which houses the disinfecting or cleaning agent or sterilization medium or cleaning medium. In another possible embodiment, the cleaning medium could comprise two separate components, which are mixed together in the spray tubes or conduits connecting the spray tubes to a reservoir before being emitted from the nozzles.

The above-discussed embodiments of the present invention will be described further herein below. When the word "invention" or "embodiment of the invention" is used in this specification, the word "invention" or "embodiment of the invention" includes "inventions" or "embodiments of the invention", that is the plural of "invention" or "embodiment of the invention". By stating "invention" or "embodiment of the invention", the Applicant does not in any way admit that the present application does not include more than one patentably and non-obviously distinct invention, and maintains that this application may include more than one patentably and non-obviously distinct invention. The Applicant hereby asserts that the disclosure of this application may include more than one invention, and, in the event that there is more than one invention, that these inventions may be patentable and non-obvious one with respect to the other.

BRIEF DESCRIPTION OF THE DRAWINGS

The present application is explained in greater detail below with reference to the one possible embodiment illustrated in the accompanying drawings, in which:

FIG. 1 is a schematic illustration of an apparatus for the treatment of containers;

FIG. 2B shows an overhead view of another embodiment of the cover apparatus;

FIG. 5 shows one embodiment of the present application with a reservoir and a bottle holder inverting arrangement;

FIG. 7 shows one embodiment of the present application in use with a linear machine;

FIG. 8 shows a block diagram of a linear beverage bottle or container cleaning or sterilizing machine with the apparatus of the present application.

DESCRIPTION OF EMBODIMENT OR EMBODIMENTS

Figure 2:
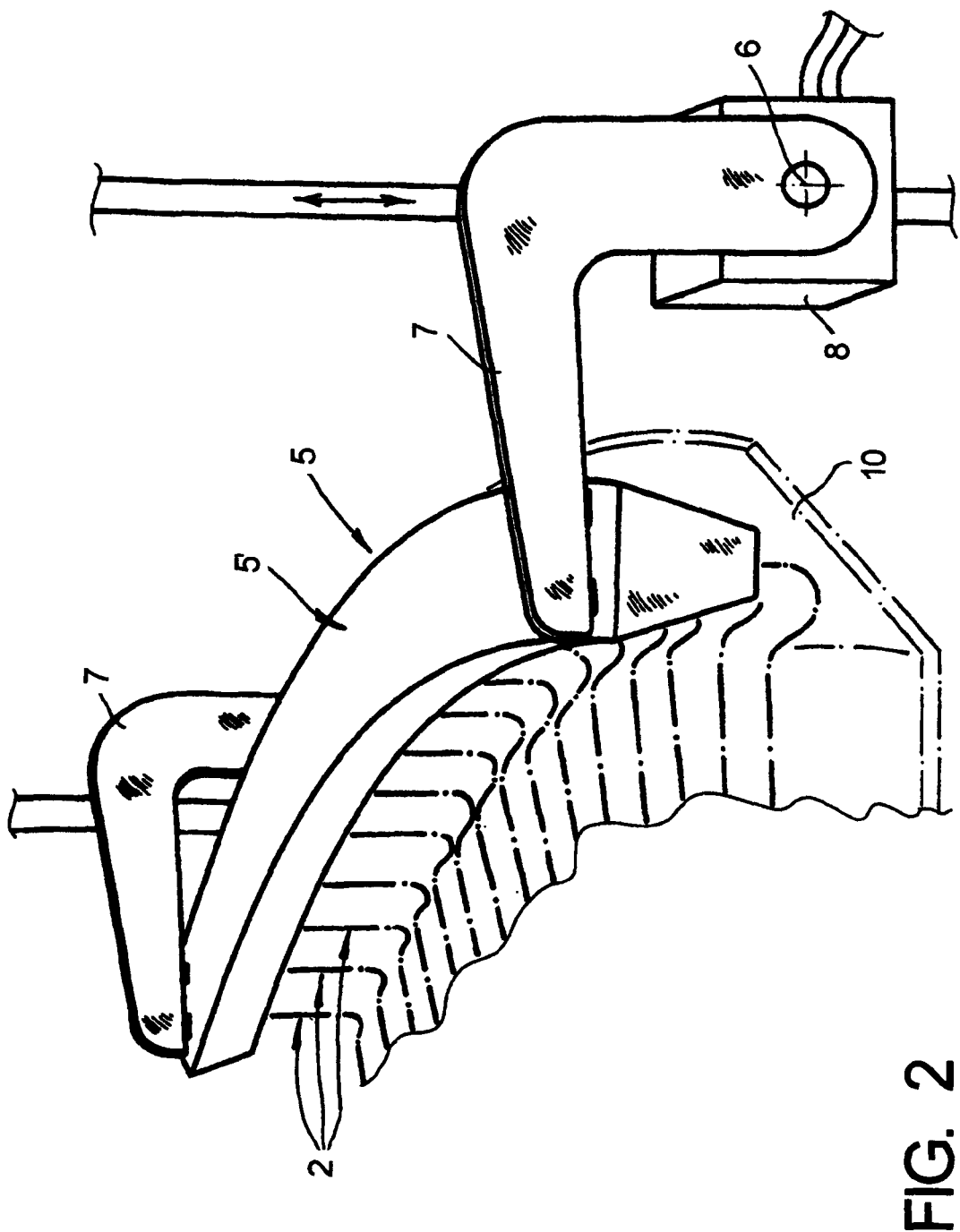
FIG. 2 is an overhead view of the cover apparatus.

The figures illustrate an apparatus for the treatment of containers 1. In this case, the containers 1 are bottles 1, although the type of container is not limited to bottles. The apparatus has a spray tube or conduit 2 with a nozzle 3 on the end. By means of the spray tube or conduit 2, the interior of the bottle or container is sprayed with a disinfecting/cleaning agent 4 for rinsing, cleaning and sterilization.

The figures also show a cover apparatus 5 which is connected to a lever 7 which can pivot around an axis of rotation 6. The cover apparatus 5 functions as a container replacement, dummy container, and/or bottle replacement and, as illustrated in FIGS. 3 and 4, is used for the circulation of the disinfecting/cleaning agent 4 during a plant cleaning, although such use is not a requirement of the present application or may not be desired.

Figure 3:
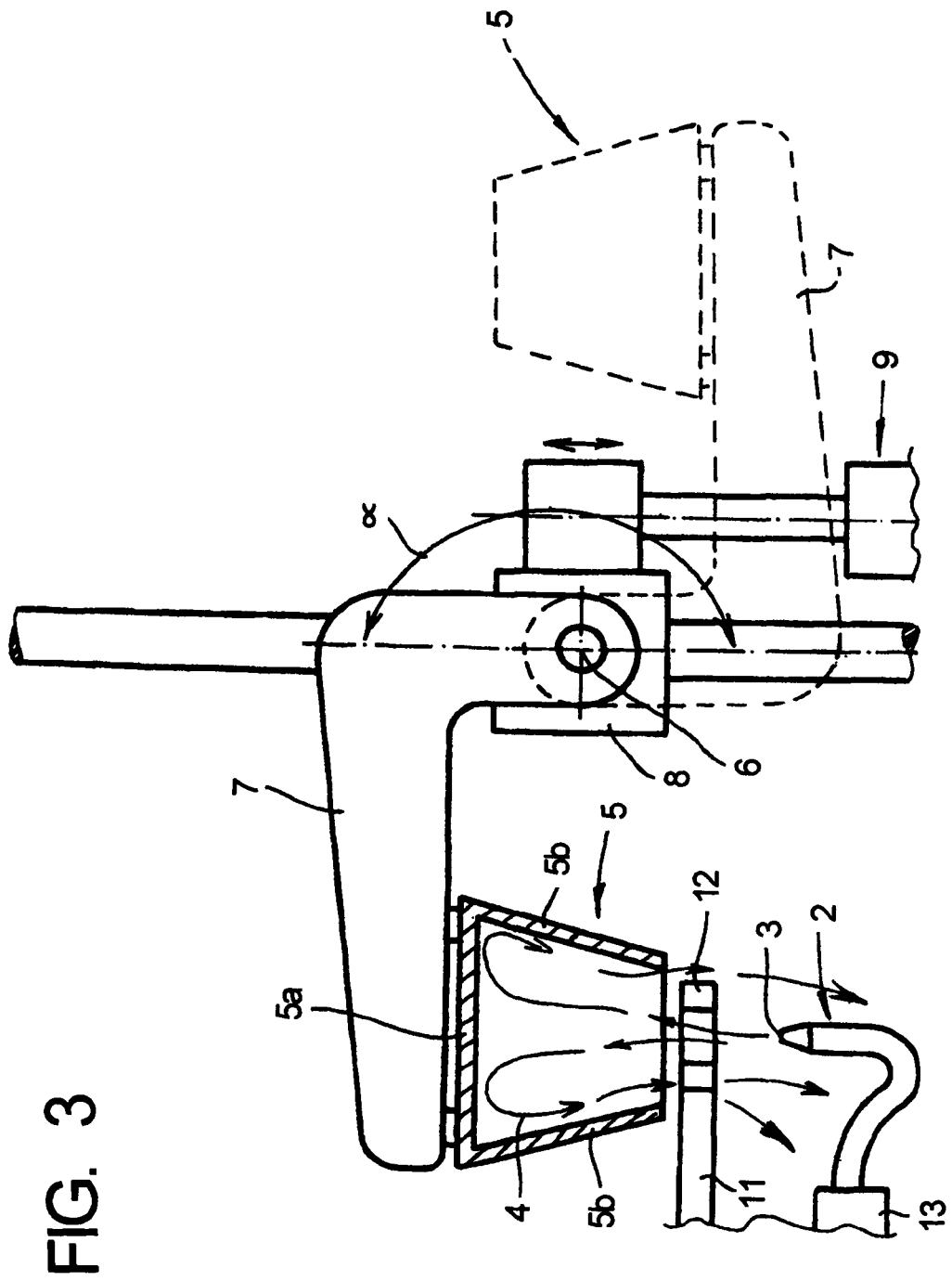
FIG. 3 is a detail from FIG. 1 showing the cover apparatus in the operating position (in solid lines) and the idle position (broken lines)
Figure 4:
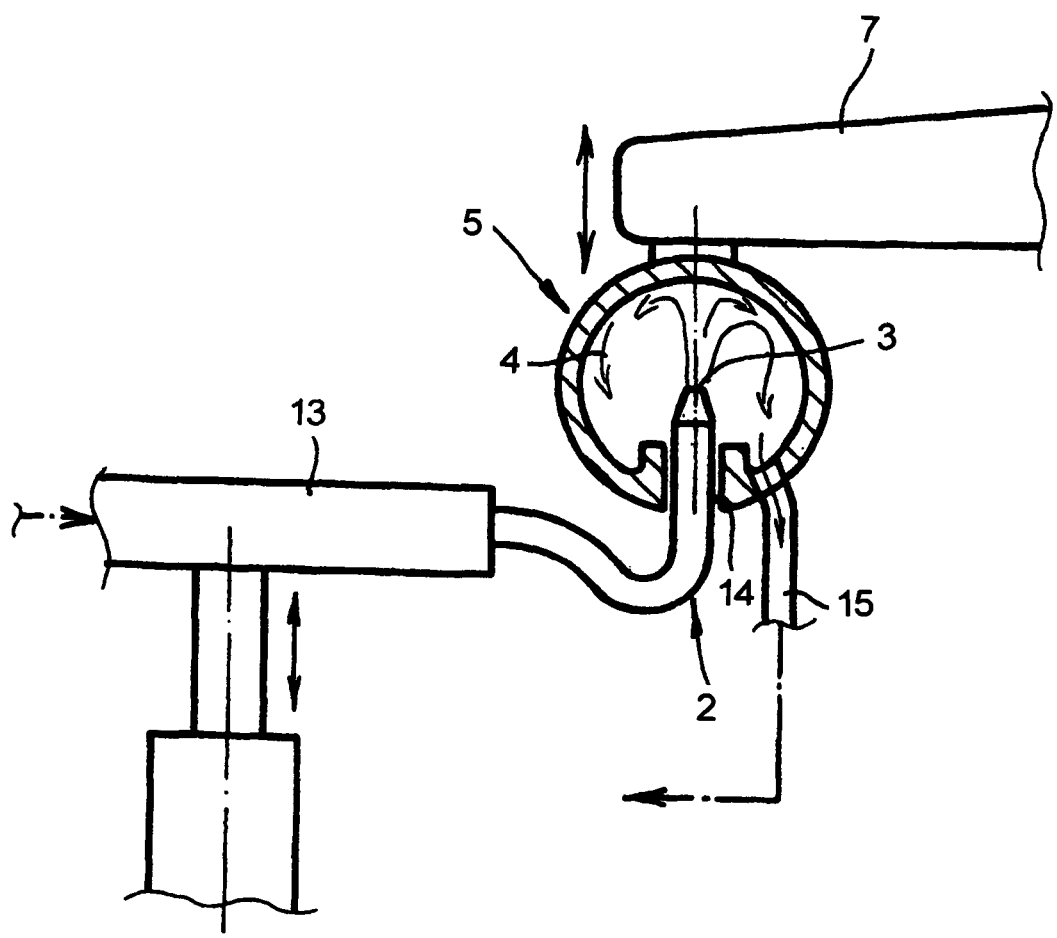
FIG. 4 is a variant of the apparatus with a modified cover apparatus.

The present application teaches that the cover apparatus 5 in question is pivoted by a motor, and namely from an idle position which is illustrated in broken lines in FIG. 3 into an operating position which is illustrated in solid lines and back again. For this purpose, a drive motor 8 is provided, which in this case is realized in the form of a rotary drive or in the form of a rotating drive motor, and is engaged directly on the axis of rotation 6 of the pivoting lever 7 or defines the axis of rotation 6 with its output shaft.

Figure 2A:
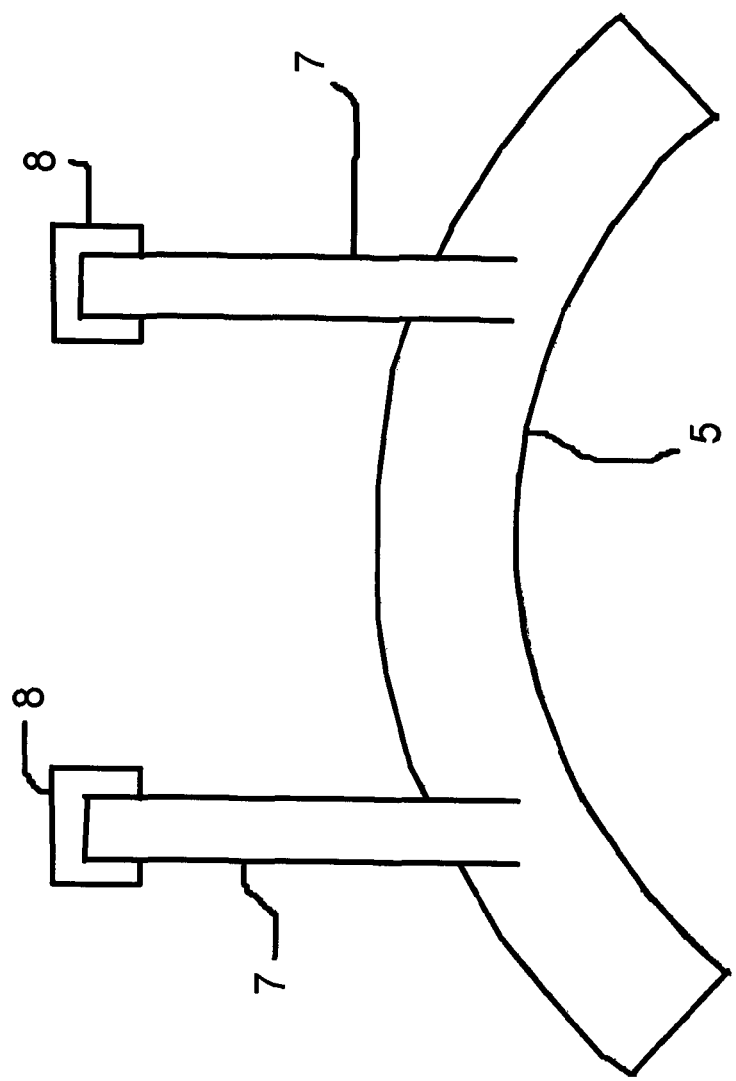
FIG. 2A shows an overhead view of one embodiment of the cover apparatus.

FIG. 2A shows one possible embodiment of the present application, in which the cover apparatus 5 is attached to two levers 7, which are each connected to a motor 8. The motors 8 are activated synchronously or individually in order to pivot both of the levers 7, thereby moving the cover apparatus 5 in a fluid, stable manner between the idle position, with the cover apparatus 5 moved pivoted away from the nozzles 3, and the working position, with the cover apparatus 5 disposed over the nozzles 3.

FIG. 2B shows another possible embodiment of the present application, in which the cover apparatus 5 is attached to a single lever 7, which is connected to a single motor 8. When the motor 8 is activated, the lever 7 is pivoted and the cover apparatus 5 is moved between the idle position and the working position.

The pivotable lever 7 is a one-armed lever, on the end of which are the drive motor 8 and the axis of rotation 6. During the change from the idle position into the operating position and back, the pivotable lever 7 and consequently the cover apparatus 5 travel over an angle α of approximately one hundred eighty degrees. Of course, other angles α are also conceivable (see FIG. 3).

FIG. 3 shows that the cover apparatus 3 is realized so that it is vertically or substantially vertical adjustable and can therefore be at a variable distance from the nozzle 3 and consequently the spray tube 2 overall. For that purpose the cover apparatus 5 is also connected to an actuator 9, which in this case can be realized in the form of a pneumatic cylinder. The actuator 9 is fastened to the pivotable lever 7 or to a separate support device which is shown in FIG. 3.

The cover apparatus 5 is realized in an overall curved shape and has at least one curved leg 5' which runs in the direction of a collecting basin 10, which is seen in FIG. 2. In its operating position, in fact, the cover apparatus 5 is located above the spray tube 2 to which the collecting basin 10 is connected underneath. FIG. 3 shows that the disinfecting/cleaning agent 4 that is discharged from the nozzle 3 of the spray tube 2 in the operating position strikes a base 5a of the cover apparatus 5 which is realized with a cross section essentially in the shape of an inverted U. In addition to this base 5a, the cover apparatus 5 in cross section has two lateral boundary legs 5b, to which the disinfecting/cleaning agent 4—beginning from the base 5a—is transported in essentially two arcs.

On the base side of the boundary legs 5b, the disinfecting/cleaning agent 4, the cover apparatus 5 and, in the illustrated embodiment and not limited to the illustrated embodiment, actuates a pivoting apparatus 11 for the individual bottles 1 for the assumption of its upside-down position, plus a retaining ring 12 for the mouth of the bottle 1 and of course the bottle 3 and the spray tube 2 as a whole, as well as an optional mounting 13 for the spray tube 2. In this manner, the above mentioned plant cleaning takes place, whereby by means of the cover apparatus 5 in the form of a container replacement, the disinfecting/cleaning agent 4 is carried in the circuit. However, that arrangement is not obligatory or may not be desired.

In the variant illustrated in FIG. 4, the cover apparatus 5 has a closed cross section, except for an opening 14 for the introduction of the nozzle 3 of the spray tube 2. To recover the disinfecting/cleaning agent 4, at this point a return line 15 is realized, which is connected to the cover apparatus 5. The figures show that in this case and otherwise, the spray tube 2 is realized so that it is vertically variable, and for this purpose has a height adjustment for the mounting 13.

FIG. 5 shows an embodiment of the present application similar to that which is seen in FIG. 1. In the embodiment illustrated in FIG. 5, the nozzle 3 and spray tube 2 are connected to a reservoir 20, which is filled with cleaning medium or sterilization medium 4, by a conduit 20a. The cleaning or sterilization medium 4 in the reservoir 20 flow through the conduits 20a, the spray tubes 2, and to the nozzles 3 in order to be discharged into the bottles 1.

Also seen in FIG. 5 is an inverting arrangement 21, which is activated to invert the bottles or containers 1 in the sterilization machine. In other embodiments according to the present application, the inverting arrangement 21 may be realized as a guide arm, which inverts bottles or containers 1 as they pass by, or the inverting arrangement could be realized as a motorized unit attached to each bottle holder or retaining ring 12 in order to activate the pivoting arrangement 11.

Figure 6:
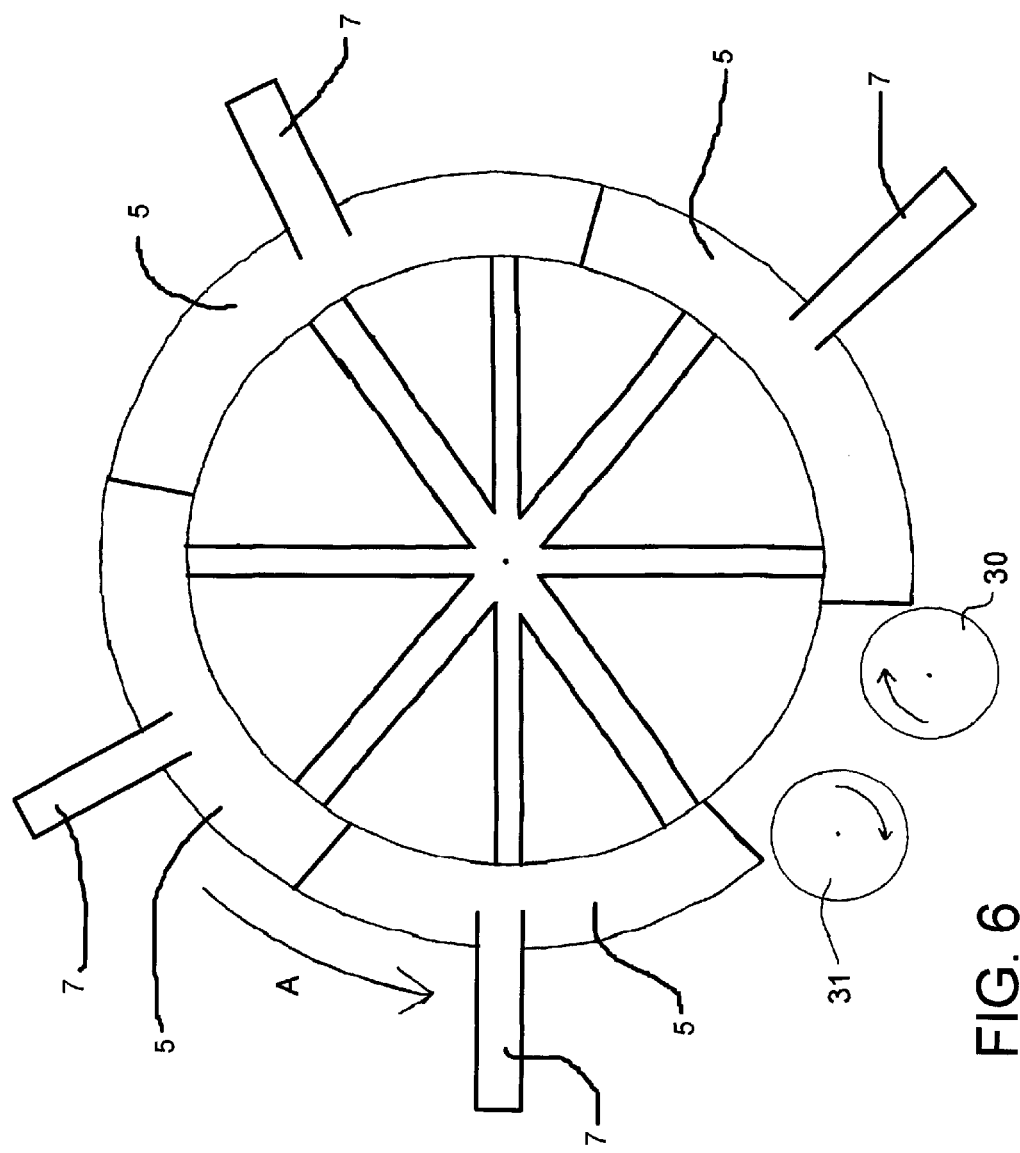
FIG. 6 shows a rotary machine including several cover apparatus of the present application.

FIG. 6 shows a rotary beverage bottle or container handling machine for the sterilization and/or cleaning of bottles or containers, with the addition of an inlet 30 and an outlet 31. In this embodiment, the rotary machine is equipped with four of the cover apparatus 5. In FIG. 6, each of the cover apparatus 5 are in the working position, i.e. disposed over the nozzles 3 in order to deflect sterilization/cleaning medium 4 back onto the nozzles 3 and other parts of the rotary machine.

Figure 6A:
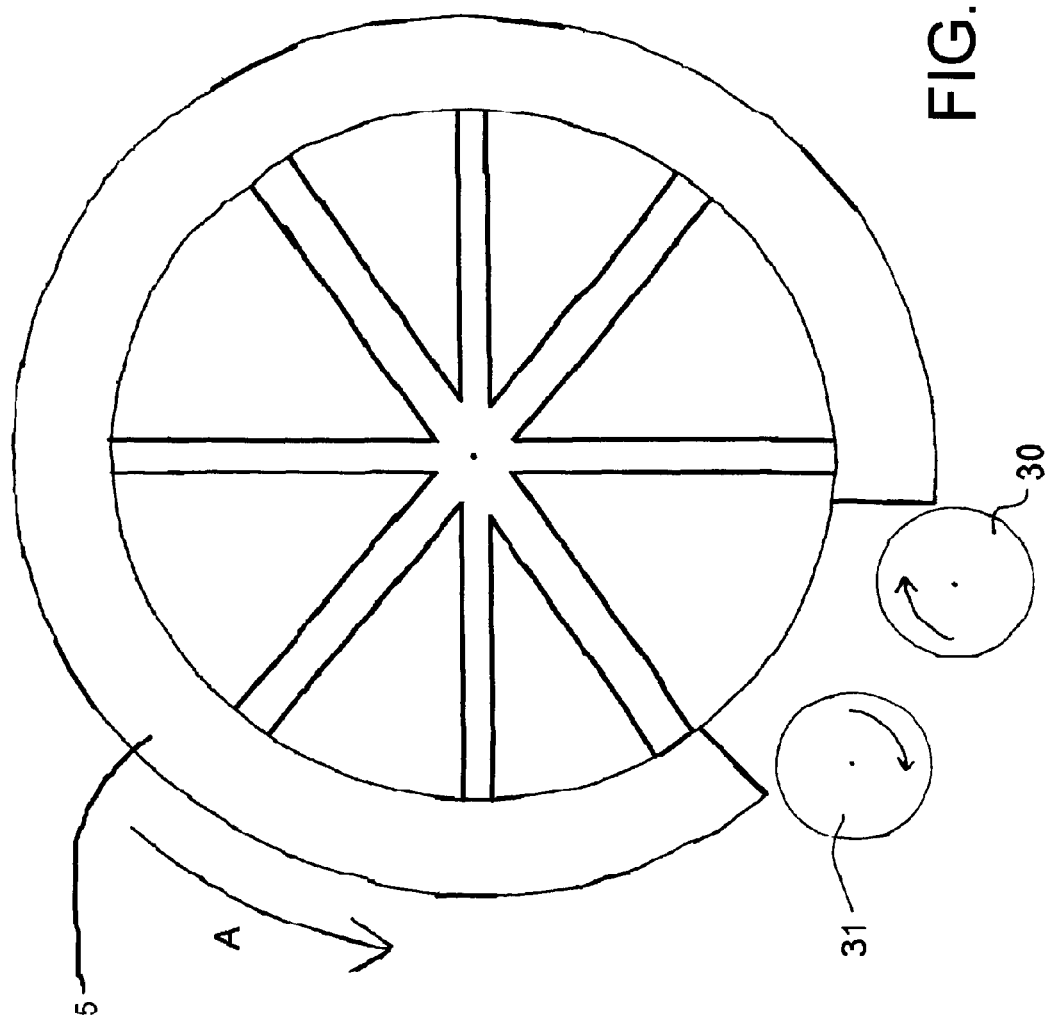
FIG. 6A shows a rotary machine including one cover apparatus of the present application.

FIG. 6A shows another possible embodiment of the present application in use with a rotary beverage bottle or container handling machine for the sterilization and/or cleaning of bottles or containers. with the addition of an inlet 30 and an outlet 31. In this embodiment, the rotary machine is equipped with one cover apparatus or deflecting structure or deflecting apparatus 5. In FIG. 6A, the cover apparatus 5 extends from the inlet 30 to the outlet 31 and is sufficiently long to cover the nozzles 3 between the inlet 30 and the outlet 31 in the working position.

FIG. 7 shows one possible embodiment of the present application in use with a linear beverage bottle or container handling machine for the sterilization and/or cleaning of beverage bottles or containers. In this embodiment for a linear machine, one cover apparatus 105 extends from the inlet 130 to the outlet 131 and is sufficiently long to cover the nozzles 3 between the inlet 130 and the outlet 131 in the working position.

FIG. 8 shows a block diagram of a linear bottle cleaning machine. The bottles or container enter through the inlet 130 and enter the cleaning machine 150. The cleaning medium deflector or cover apparatus 105 is disposed off the cleaning machine 150 in an idle position. The bottles, once cleaned and/or sterilized and/or disinfected, then exit the cleaning machine 150 through the outlet 131.

Figure 9:
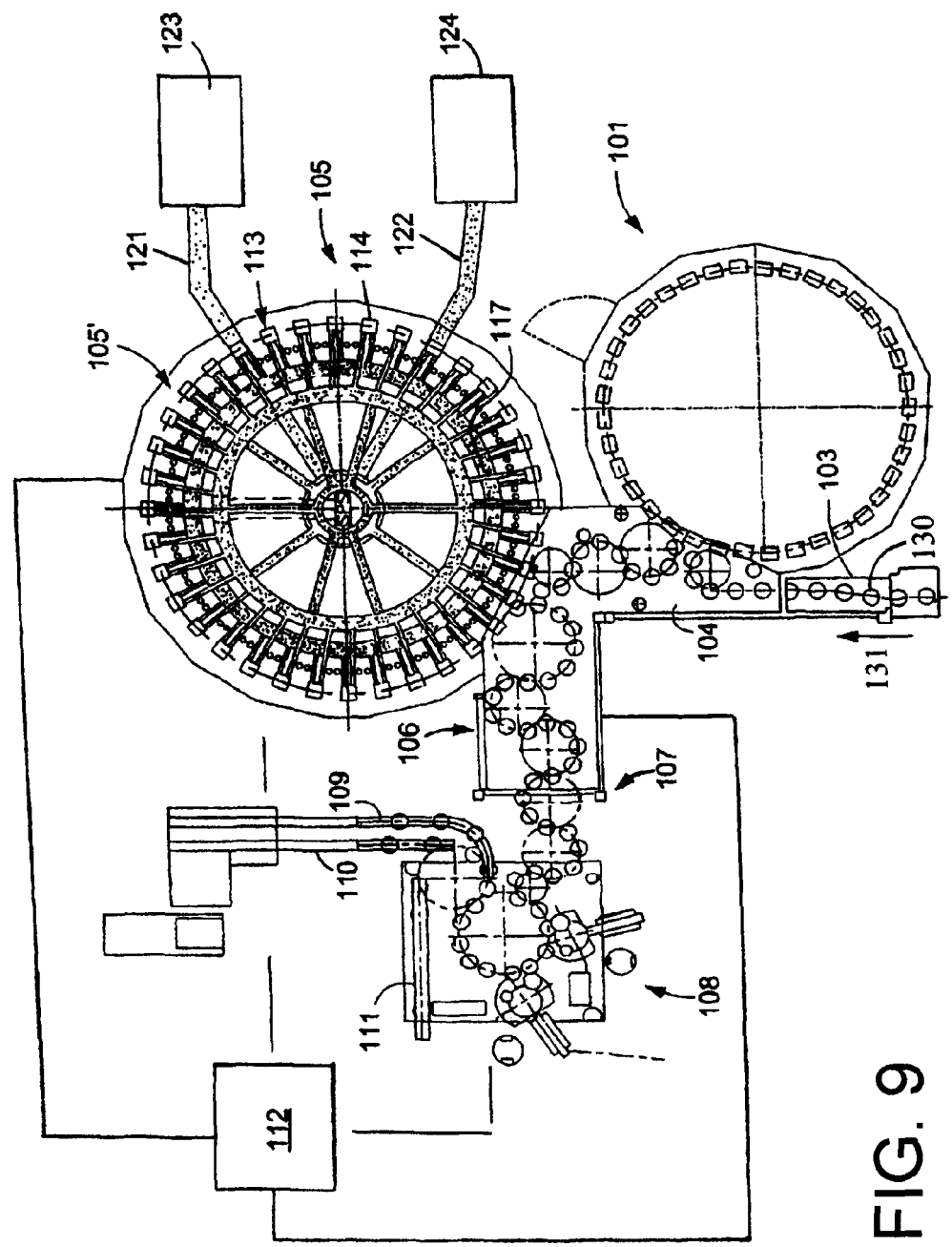
FIG. 9 shows schematically the main components of one possible embodiment example of a system for filling containers, specifically, a beverage bottling plant for filling bottles with at least one liquid beverage, in accordance with at least one possible embodiment, in which system or plant could possibly be utilized at least one aspect, or several aspects, of the embodiments disclosed herein.

FIG. 9 shows schematically the main components of one possible embodiment example of a system for filling containers, specifically, a beverage bottling plant for filling bottles with at least one liquid beverage, in accordance with at least one possible embodiment, in which system or plant could possibly be utilized at least one aspect, or several aspects, of the embodiments disclosed herein.

FIG. 9 shows a rinsing arrangement or rinsing station, cleaning machine, sterilizing machine, or disinfecting machine 101, to which the containers, namely bottles 130, are fed in the direction of travel as indicated by the arrow 131, by a first conveyor arrangement 103, which can be a linear conveyor or a combination of a linear conveyor and a starwheel. Downstream of the rinsing arrangement or rinsing station 101, in the direction of travel as indicated by the arrow 131, the rinsed bottles 130 are transported to a beverage filling machine 105 by a second conveyor arrangement 104 that is formed, for example, by one or more starwheels that introduce bottles 130 into the beverage filling machine 105.

In at least one possible embodiment of the present application, the rinsing arrangement or station, cleaning machine, sterilizing machine, or disinfecting machine 101 comprises the cover apparatus 5 of the present application.

The beverage filling machine 105 shown is of a revolving or rotary design, with a rotor 105', which revolves around a central, vertical machine axis. The rotor 105' is designed to receive and hold the bottles 130 for filling at a plurality of filling positions 113 located about the periphery of the rotor 105'. At each of the filling positions 103 is located a filling arrangement 114 having at least one filling device, element, apparatus, or valve. The filling arrangements 114 are designed to introduce a predetermined volume or amount of liquid beverage into the interior of the bottles 130 to a predetermined or desired level.

The filling arrangements 114 receive the liquid beverage material from a toroidal or annular vessel 117, in which a supply of liquid beverage material is stored under pressure by a gas. The toroidal vessel 117 is a component, for example, of the revolving rotor 105'. The toroidal vessel 117 can be connected by means of a rotary coupling or a coupling that permits rotation. The toroidal vessel 117 is also connected to at least one external reservoir or supply of liquid beverage material by a conduit or supply line. In the embodiment shown in FIG. 9, there are two external supply reservoirs 123 and 124, each of which is configured to store either the same liquid beverage product or different products. These reservoirs 123, 124 are connected to the toroidal or annular vessel 117 by corresponding supply lines, conduits, or arrangements 121 and 122. The external supply reservoirs 123, 124 could be in the form of simple storage tanks, or in the form of liquid beverage product mixers, in at least one possible embodiment.

As well as the more typical filling machines having one toroidal vessel, it is possible that in at least one possible embodiment there could be a second toroidal or annular vessel which contains a second product. In this case, each filling arrangement 114 could be connected by separate connections to each of the two toroidal vessels and have two individually-controllable fluid or control valves, so that in each bottle 130, the first product or the second product can be filled by means of an appropriate control of the filling product or fluid valves.

Downstream of the beverage filling machine 105, in the direction of travel of the bottles 130, there can be a beverage bottle closing arrangement or closing station 106 which closes or caps the bottles 130. The beverage bottle closing arrangement or closing station 106 can be connected by a third conveyor arrangement 107 to a beverage bottle labeling arrangement or labeling station 108. The third conveyor arrangement may be formed, for example, by a plurality of starwheels, or may also include a linear conveyor device.

In the illustrated embodiment, the beverage bottle labeling arrangement or labeling station 108 has at least one labeling unit, device, or module, for applying labels to bottles 130. In the embodiment shown, the labeling arrangement 108 is connected by a starwheel conveyor structure to three output conveyor arrangements: a first output conveyor arrangement 109, a second output conveyor arrangement 110, and a third output conveyor arrangement 111, all of which convey filled, closed, and labeled bottles 130 to different locations.

The first output conveyor arrangement 109, in the embodiment shown, is designed to convey bottles 130 that are filled with a first type of liquid beverage supplied by, for example, the supply reservoir 123. The second output conveyor arrangement 110, in the embodiment shown, is designed to convey bottles 130 that are filled with a second type of liquid beverage supplied by, for example, the supply reservoir 124. The third output conveyor arrangement 111, in the embodiment shown, is designed to convey incorrectly labeled bottles 130. To further explain, the labeling arrangement 108 can comprise at least one beverage bottle inspection or monitoring device that inspects or monitors the location of labels on the bottles 130 to determine if the labels have been correctly placed or aligned on the bottles 130. The third output conveyor arrangement 111 removes any bottles 130 which have been incorrectly labeled as determined by the inspecting device.

The beverage bottling plant can be controlled by a central control arrangement 112, which could be, for example, computerized control system that monitors and controls the operation of the various stations and mechanisms of the beverage bottling plant.

The apparatus according to the present application to accomplish this object is configured so that the cover apparatus 5 is equipped with a lever 7 which can pivot around an axis of rotation 6. The pivotable lever 7 is pivoted by a motor from an idle position into an operating position and back. The cover apparatus 5 is realized so that its height is variable with reference to the spray tube 2. For this purpose, the cover apparatus 5 is connected to an actuator 9.

In addition, the altitude of the overall cover apparatus 5 according to the present application can be adjusted, and for this purpose is equipped with an additional actuator. It is now possible, depending on the consistency (viscosity), pressure, flow velocity, nozzle used, etc., to adapt the "height" of the cover apparatus 5 above the spray nozzle 3 or the spray tube 2 to local conditions.

For example, if the cleaning fluid 4 used is relatively viscous, the cover apparatus 5 is attached in the immediate or general vicinity of the nozzle 3 to be able to distribute the cleaning agent uniformly. If, on the other hand in one possible embodiment, the cleaning agent 4 has a relatively low viscosity, a relatively elevated position of the cover apparatus 5 is used to prevent, restrict, and/or minimize uncontrolled spraying.

It is further possible to adapt the cover apparatus 5 to the current conditions, and in one possible embodiment depending on whether a comprehensive cleaning is desired or not. In this case, too, the variable height of the cover apparatus 5 takes the current requirements or desires into consideration. For example, a cover apparatus 5 in a "low" position corresponds to a cleaning spray that is directed backward, while a "high" position encourages a superficial cleaning. Apart from that, a design of this type provides the basic capability of retrofitting the cover device on existing equipment and thereby taking into consideration altogether different designs of the container handling machine.

An object of the present application is an apparatus for the treatment of containers 1, in one possible embodiment for the upside-down cleaning of bottles 1. In its basic configuration, this present application is equipped with a spray tube 2 to spray the interior of the container with a disinfecting/cleaning agent 4. A cover apparatus 5 is also realized as a container replacement for the possible circulation of the disinfecting/cleaning agent 4 during a plant cleaning. The present application teaches that the cover apparatus 5 can be pivoted by a motor from an idle position into an operating position and back.

One feature or aspect of an embodiment is believed at the time of the filing of this patent application to possibly reside broadly in an apparatus for the treatment of containers 1, in one possible embodiment for the upside-down cleaning of bottles 1, with a spray tube 2 to spray the interior of the container with a disinfecting/cleaning agent 4 and with a cover apparatus 5 as a container replacement for the possible circulation of the disinfecting/cleaning agent 4 during a plant cleaning, wherein the cover apparatus 5 can be pivoted by a motor from an idle position into an operating position and back.

Another feature or aspect of an embodiment is believed at the time of the filing of this patent application to possibly reside broadly in the apparatus, wherein the cover apparatus 5 is connected to a lever 7, in one possible embodiment a one-armed lever, which can be pivoted around an axis of rotation 6.

Yet another feature or aspect of an embodiment is believed at the time of the filing of this patent application to possibly reside broadly in the apparatus, wherein a drive motor 8 is provided which is engaged on the axis of rotation 6 or defines the axis of rotation 6.

Still another feature or aspect of an embodiment is believed at the time of the filing of this patent application to possibly reside broadly in the apparatus, wherein the cover apparatus 5 is realized at a variable distance from a nozzle 3 of the spray tube 2.

A further feature or aspect of an embodiment is believed at the time of the filing of this patent application to possibly reside broadly in the apparatus, wherein the cover apparatus 5 has an overall curved shape with at least one curved leg 5' that is directed toward a collecting basin 10.

Another feature or aspect of an embodiment is believed at the time of the filing of this patent application to possibly reside broadly in the apparatus, wherein the cover apparatus 5 is realized with a cross section essentially in the shape of an inverted U with a base 5a and at least two lateral boundary legs 5b.

Yet another feature or aspect of an embodiment is believed at the time of the filing of this patent application to possibly reside broadly in the apparatus, wherein the cover device 5 is realized with a closed cross section except for an introduction opening 14 for the nozzle 3 of the spray tube 2.

Still another feature or aspect of an embodiment is believed at the time of the filing of this patent application to possibly reside broadly in the apparatus, wherein the spray tube 2 is connected to a variable-height retaining apparatus 13.

A further feature or aspect of an embodiment is believed at the time of the filing of this patent application to possibly reside broadly in the apparatus, wherein the cover apparatus 5 has a return line 15 for the disinfecting/cleaning agent 4.

One feature or aspect of an embodiment is believed at the time of the filing of this patent application to possibly reside broadly in the apparatus, wherein the cover apparatus 5 covers an angle α of approximately one hundred eighty degrees during the movement from the idle position into the operating position and back.

Another feature or aspect of an embodiment is believed at the time of the filing of this patent application to possibly reside broadly in an apparatus for the treatment of containers 1, in one possible embodiment for the upside-down cleaning of bottles 1, with a spray tube 2 to spray the interior of the container with a disinfecting/cleaning agent 4 and with a cover apparatus 5 as a container replacement for the possible circulation of the disinfecting/cleaning agent 4 during a plant cleaning, wherein the cover apparatus 5 is connected to a lever 7 that can pivot around an axis of rotation 6 and can be pivoted by a motor from an idle position into an operating position and back, and that the cover apparatus 5 is vertically adjustable with reference to the spray tube 2 and is also connected to an actuator 9.

Yet another feature or aspect of an embodiment is believed at the time of the filing of this patent application to possibly reside broadly in the apparatus, wherein the actuator 9 is realized in the form of a pneumatic cylinder.

Still another feature or aspect of an embodiment is believed at the time of the filing of this patent application to possibly reside broadly in the apparatus, wherein a drive motor 8 is provided which is engaged with the axis of rotation 6 or defines the axis of rotation 6.

A further feature or aspect of an embodiment is believed at the time of the filing of this patent application to possibly reside broadly in the apparatus, wherein the lever 7 is realized in the form of a one-armed lever.

Another feature or aspect of an embodiment is believed at the time of the filing of this patent application to possibly reside broadly in the apparatus, wherein the cover apparatus 5 has an overall curved shape with at least one curved leg 5' that is directed toward a collecting basin 10.

Yet another feature or aspect of an embodiment is believed at the time of the filing of this patent application to possibly reside broadly in the apparatus, wherein the cover apparatus 5 is realized with a cross section essentially in the shape of an inverted U with a base 5a and at least two lateral boundary legs 5b.

Still another feature or aspect of an embodiment is believed at the time of the filing of this patent application to possibly reside broadly in the apparatus, wherein the cover device 5 is realized with a closed cross section except for an introduction opening 14 for the nozzle 3 of the spray tube 2.

A further feature or aspect of an embodiment is believed at the time of the filing of this patent application to possibly reside broadly in the apparatus, wherein the cover apparatus 5 has a return line 15 for the disinfecting/cleaning agent 4.

One feature or aspect of an embodiment is believed at the time of the filing of this patent application to possibly reside broadly in a rotary beverage bottle cleaning and/or disinfecting machine for the cleaning and/or disinfecting of at least interiors of beverage bottles disposed upside-down in a beverage bottle filling plant, which rotary beverage bottle cleaning and/or disinfecting machine is also configured to clean and/or disinfect said rotary beverage bottle cleaning and/or disinfecting machine during a plant cleaning and/or disinfecting; said rotary beverage bottle cleaning and/or disinfecting machine comprising: a rotary beverage bottle cleaning and/or disinfecting machine frame; a plurality of beverage bottle holders being configured and disposed to hold beverage bottles disposed upside-down; an inverting arrangement being configured and disposed to invert beverage bottles; a plurality of nozzles being configured and disposed to discharge cleaning and/or disinfecting medium in an upward direction; said plurality of nozzles being further configured and disposed to discharge cleaning and/or disinfecting medium in an upward direction into interiors of beverage bottles disposed upside-down to clean and/or disinfect at least the interiors of beverage bottles; a reservoir being configured and disposed to house a cleaning and/or disinfecting medium; a plurality of conduits being configured and disposed to connect each of said plurality of nozzles to said reservoir and permit the flow of cleaning and/or disinfecting medium from said reservoir to said plurality of nozzles; a plurality of deflecting apparatus being configured and disposed to deflect cleaning and/or disinfecting medium being discharged from said plurality of nozzles back toward said plurality of nozzles and toward at least a portion of said inverting arrangement, said plurality of beverage bottle holders, said rotary beverage bottle cleaning and/or disinfecting machine frame, and said plurality of conduits in order to clean and/or disinfect said rotary beverage bottle cleaning and/or disinfecting machine; each of said plurality of deflecting apparatus being configured to clean and/or disinfect a portion of said plurality of nozzles, a portion of said inverting arrangement, a portion of said plurality of beverage bottle holders, a portion of said rotary beverage bottle cleaning and/or disinfecting machine frame, and a portion of said plurality of conduits; each of said plurality of deflecting apparatus comprising: a vertical structure being configured and disposed to support said deflecting apparatus; a deflecting structure comprising: a flat base; two sides being at least substantially transverse to said flat base; a lever being configured and disposed to connect said deflecting structure to said vertical structure and being further configured to pivot about an axis of rotation of said lever; a motor being configured and disposed to: rotate said lever about said axis of rotation; and pivot said lever and said deflecting structure between an idle position with said deflecting structure being disposed away from said portion of said plurality of nozzles, during cleaning and/or disinfecting of at least interiors of beverage bottles, and a working position with said deflecting structure being disposed above said portion of said plurality of nozzles, during plant cleaning and/or disinfecting; an actuating device being configured and disposed to adjust the vertical height of said deflecting structure, upon said deflecting structure being in the working position, and change the distance between said portion of said plurality of nozzles and said deflecting structure.

Another feature or aspect of an embodiment is believed at the time of the filing of this patent application to possibly reside broadly in the rotary beverage bottle cleaning and/or disinfecting machine, wherein: said plurality of nozzles is further configured to discharge sterilization medium; and said plurality of conduits is further configured to permit the flow of sterilization medium.

Yet another feature or aspect of an embodiment is believed at the time of the filing of this patent application to possibly reside broadly in the rotary beverage bottle cleaning and/or disinfecting machine, wherein said lever comprises a one-armed lever.

Still another feature or aspect of an embodiment is believed at the time of the filing of this patent application to possibly reside broadly in the rotary beverage bottle cleaning and/or disinfecting machine, wherein said rotary beverage bottle cleaning and/or disinfecting machine further comprises a collecting basin being configured and disposed to collect deflected cleaning and/or disinfecting medium below said plurality of nozzles.

A further feature or aspect of an embodiment is believed at the time of the filing of this patent application to possibly reside broadly in the container cleaning machine, wherein said deflecting structure further comprises: an opening disposed between said two sides and substantially opposite said flat base and is configured to permit cleaning and/or disinfecting medium to enter said deflecting structure; and a substantially U-shaped cross-section.

Another feature or aspect of an embodiment is believed at the time of the filing of this patent application to possibly reside broadly in the rotary beverage bottle cleaning and/or disinfecting machine, wherein said deflecting structure is configured to be pivoted about one hundred eighty degrees between said idle position and said working position; said actuating device comprises a pneumatic cylinder; said deflecting apparatus comprises a curved portion being configured and disposed to deflect cleaning and/or disinfecting medium, being discharged from said plurality of nozzles back, into said collecting basin.

Still another feature or aspect of an embodiment is believed at the time of the filing of this patent application to possibly reside broadly in a container cleaning machine, in a container filling plant, for the cleaning of containers disposed upside-down, which container cleaning machine is also configured to clean said container cleaning machine during a plant cleaning; said container cleaning machine comprising: a container handling machine frame; at least one container holder being configured and disposed to hold at least one container disposed upside-down; at least one nozzle being configured and disposed to discharge cleaning medium in an upward direction and into at least one container disposed upside-down to clean at least one container; at least one conduit being configured and disposed to connect said at least one nozzle to a source of cleaning medium and permit the flow of cleaning medium from a source to said at least one nozzle; a deflecting apparatus comprising at least one surface being configured and disposed to deflect cleaning medium being discharged from said at least one nozzle back toward said at least one nozzle and toward at least one of: at least a portion of said at least one container holder, at least a portion of said container handling machine frame, and at least a portion of said at least one conduit in order to clean said container cleaning machine; and a moving arrangement being configured and disposed to move said deflecting structure between an idle position with said deflecting structure being disposed away from said portion of said at least one nozzle, during cleaning of containers, and a working position with said deflecting structure being disposed above said portion of said at least one nozzle, during plant cleaning.

A further feature or aspect of an embodiment is believed at the time of the filing of this patent application to possibly reside broadly in the container cleaning machine, wherein said container cleaning machine is either configured as a part of a rotary beverage bottle sterilization machine or as a part of a linear beverage bottle sterilization machine.

One feature or aspect of an embodiment is believed at the time of the filing of this patent application to possibly reside broadly in the container cleaning machine, wherein: said at least one nozzle is further configured to discharge sterilization medium; and said at least one conduit is further configured to permit the flow of sterilization medium.

Another feature or aspect of an embodiment is believed at the time of the filing of this patent application to possibly reside broadly in the container cleaning machine, wherein: said at least one nozzle comprises a plurality of nozzles; and said deflecting apparatus is elongated and configured to deflect cleaning medium being discharged from at least a portion of said plurality of nozzles.

Yet another feature or aspect of an embodiment is believed at the time of the filing of this patent application to possibly reside broadly in the container cleaning machine, wherein said container cleaning machine further comprises a pivoting arrangement configured and disposed to connect said deflecting apparatus and said moving arrangement and to pivot said deflecting apparatus between said idle position and said working position, upon said moving arrangement being activated.

Still another feature or aspect of an embodiment is believed at the time of the filing of this patent application to possibly reside broadly in the container cleaning machine, wherein said pivoting arrangement comprises a one-armed lever.

A further feature or aspect of an embodiment is believed at the time of the filing of this patent application to possibly reside broadly in the container cleaning machine, wherein said container cleaning machine further comprises a collecting basin being configured and disposed to collect deflected cleaning medium below said at least one nozzle.

Another feature or aspect of an embodiment is believed at the time of the filing of this patent application to possibly reside broadly in the container cleaning machine, wherein: said at least one surface of said deflecting apparatus further comprises: a base; at least two sides substantially transverse to said base; said deflecting apparatus further comprises: an opening disposed between said at least two sides and substantially opposite said base and is configured to permit cleaning medium to enter said deflecting apparatus; and a substantially U-shaped cross-section.

Yet another feature or aspect of an embodiment is believed at the time of the filing of this patent application to possibly reside broadly in the container cleaning machine, wherein: said at least one surface of said deflecting apparatus is rounded; said rounded at least one surface comprises a substantially C-shaped cross-section with an opening; and said opening of said deflecting apparatus is configured to accept said at least one nozzle and is further configured to permit cleaning medium to enter said deflecting apparatus.

Still another feature or aspect of an embodiment is believed at the time of the filing of this patent application to possibly reside broadly in the container cleaning machine, wherein said deflecting apparatus further comprises a conduit configured and disposed to drain said deflecting apparatus of cleaning medium.

A further feature or aspect of an embodiment is believed at the time of the filing of this patent application to possibly reside broadly in the container cleaning machine, wherein said deflecting apparatus is configured to be pivoted about one hundred eighty degrees between said idle position and said working position.

One feature or aspect of an embodiment is believed at the time of the filing of this patent application to possibly reside broadly in the container cleaning machine, wherein said deflecting apparatus is configured to be pivoted about one hundred eighty degrees between said idle position and said working position.

Another feature or aspect of an embodiment is believed at the time of the filing of this patent application to possibly reside broadly in the container cleaning machine, wherein: said container cleaning machine further comprises an adjusting arrangement configured and disposed to adjust the distance between said at least one nozzle and said deflecting apparatus, upon said deflecting apparatus being in said working position; said adjusting arrangement comprises a pneumatic cylinder; said moving arrangement is configured to pivot about an axis of rotation; and said deflecting apparatus comprises a curved portion being configured and disposed to deflect cleaning medium, being discharged from said at least one nozzle back, into said collecting basin.

Yet another feature or aspect of an embodiment is believed at the time of the filing of this patent application to possibly reside broadly in the container cleaning machine, wherein: said container cleaning machine further comprises an adjusting arrangement configured and disposed to adjust the distance between said at least one nozzle and said deflecting apparatus, upon said deflecting apparatus being in said working position; said adjusting arrangement comprises a pneumatic cylinder; said moving arrangement is configured to pivot about an axis of rotation; and said deflecting apparatus comprises a curved portion being configured and disposed to deflect cleaning medium, being discharged from said at least one nozzle back, into said collecting basin.

The components disclosed in the various publications, disclosed or incorporated by reference herein, may possibly be used in possible embodiments of the present invention, as well as equivalents thereof.

The purpose of the statements about the technical field is generally to enable the Patent and Trademark Office and the public to determine quickly, from a cursory inspection, the nature of this patent application. The description of the technical field is believed, at the time of the filing of this patent application, to adequately describe the technical field of this patent application. However, the description of the technical field may not be completely applicable to the claims as originally filed in this patent application, as amended during prosecution of this patent application, and as ultimately allowed in any patent issuing from this patent application. Therefore, any statements made relating to the technical field are not intended to limit the claims in any manner and should not be interpreted as limiting the claims in any manner.

The appended drawings in their entirety, including all dimensions, proportions and/or shapes in at least one embodiment of the invention, are accurate and are hereby included by reference into this specification.

The background information is believed, at the time of the filing of this patent application, to adequately provide background information for this patent application. However, the background information may not be completely applicable to the claims as originally filed in this patent application, as amended during prosecution of this patent application, and as ultimately allowed in any patent issuing from this patent application. Therefore, any statements made relating to the background information are not intended to limit the claims in any manner and should not be interpreted as limiting the claims in any manner.

All, or substantially all, of the components and methods of the various embodiments may be used with at least one embodiment or all of the embodiments, if more than one embodiment is described herein.

The purpose of the statements about the object or objects is generally to enable the Patent and Trademark Office and the public to determine quickly, from a cursory inspection, the nature of this patent application. The description of the object or objects is believed, at the time of the filing of this patent application, to adequately describe the object or objects of this patent application. However, the description of the object or objects may not be completely applicable to the claims as originally filed in this patent application, as amended during prosecution of this patent application, and as ultimately allowed in any patent issuing from this patent application. Therefore, any statements made relating to the object or objects are not intended to limit the claims in any manner and should not be interpreted as limiting the claims in any manner.

All of the patents, patent applications and publications recited herein, and in the Declaration attached hereto, are hereby incorporated by reference as if set forth in their entirety herein.

The summary is believed, at the time of the filing of this patent application, to adequately summarize this patent application. However, portions or all of the information contained in the summary may not be completely applicable to the claims as originally filed in this patent application, as amended during prosecution of this patent application, and as ultimately allowed in any patent issuing from this patent application. Therefore, any statements made relating to the summary are not intended to limit the claims in any manner and should not be interpreted as limiting the claims in any manner.

It will be understood that the examples of patents, published patent applications, and other documents which are included in this application and which are referred to in paragraphs which state "Some examples of . . . which may possibly be used in at least one possible embodiment of the present application . . . " may possibly not be used or usable in any one or more embodiments of the application.

The sentence immediately above relates to patents, published patent applications and other documents either incorporated by reference or not incorporated by reference.

U.S. patent application Ser. No. 12/269,330, filed on Nov. 12, 2008, having inventors Herbert MENKE, Martin WEISGERBER, and Ralph POHL, and title "BOTTLE INVERTING AND BOTTLE DRAINING STATION CONFIGURED TO DRAIN RINSED BOTTLES FROM A RINSER IN A CONTAINER FILLING PLANT," and its corresponding Federal Republic of Germany Patent Application No. 10 2006 022 465.5, filed on May 13, 2006, and International Patent Application No. PCT/EP2007004178, filed on May 11, 2007, having WIPO Publication No. WO 2007/131713 and inventors Herbert MENKE, Martin WEISGERBER, and Ralph POHL are hereby incorporated by reference as if set forth in their entirety herein.

The Innoclean SEC bottle washing machine, manufactured by KHS AG, is an example of a bottle handling machine with a guide arm for inverting bottles, which may possibly be utilized or adapted for use in at least one possible embodiment. Some other examples of bottle handling machines with guide arms for inverting bottles which may possibly be utilized or adapted for use in at least one possible embodiment, which are also manufactured by KHS AG, may include: the Innoclean FR-ZR, the Innoclean FR-DR, the Innoclean FR-ZM, and the Innoclean FR-EM.

The following patents, patent applications or patent publications, are hereby incorporated by reference as if set forth in their entirety herein: DE 299 03 939 U1, having the following German title "VORRICHTUNG ZUR ÜBERKOPF-BEHANDLUNG VON FLASCHEN," published on Apr. 20, 2000.

All of the patents, patent applications or patent publications, which were cited in the International Search report dated Aug. 6, 2008, and/or cited elsewhere are hereby incorporated by reference as if set forth in their entirety herein as follows: DE 44 25 219, having the following English translation of the German title "CLEANING AND STERILISING BOTTLE FILLING MACHINE," published on Jan. 18, 1996; DE 198 24 991, having the following English translation of the German title "CLEANING DEVICE FOR E.G. MEAT CUTTING OR MINCING MACHINERY," published on Dec. 16, 1999; EP 1,281,446, having the title "MEASURING DEVICE FOR MONITORING THE CLEANING OF CONTAINERS IN A WASHING INSTALLATION," published on Feb. 5, 2003; U.S. Pat. No. 5,409,545, having the title "APPARATUS AND METHOD FOR CLEANING CONTAINERS," published on Apr. 25, 1995; and US 2003/188769, having the title "APPLIANCE FOR TREATING ARTICLES, PARTICULARLY NURSING BOTTLES AND ACCESSORIES," published on Oct. 9, 2003.

The patents, patent applications, and patent publication listed above, beginning on line 925 on page 45 in the paragraph with the phrase: "U.S. patent application Ser. No. 12/269,330 . . ." and ending on line 966 on page 46 in the paragraph with the phrase: ". . . published on Oct. 9, 2003," are herein incorporated by reference as if set forth in their entirety. The purpose of incorporating U.S. patents, Foreign patents, publications, etc. is solely to provide additional information relating to technical features of one or more embodiments, which information may not be completely disclosed in the wording in the pages of this application. Words relating to the opinions and judgments of the author and not directly relating to the technical details of the description of the embodiments therein are not incorporated by reference. The words all, always, absolutely, consistently, preferably, guarantee, particularly, constantly, ensure, necessarily, immediately, endlessly, avoid, exactly, continually, expediently, need, must, only, perpetual, precise, perfect, require, requisite, simultaneous, total, unavoidable, and unnecessary, or words substantially equivalent to the above-mentioned words in this sentence, when not used to describe technical features of one or more embodiments, are not considered to be incorporated by reference herein.

The corresponding foreign and international patent publication applications, namely, Federal Republic of Germany Patent Application No. 10 2006 038 255.2, filed on Aug. 16, 2006, having inventors Steffen KAPPEL and Klaus BAUMGARTNER, and DE-OS 10 2006 038 255.2 and DE-PS 10 2006 038 255.2, and International Application No. PCT/EP2007/007188, filed on Aug. 15, 2007, having WIPO Publication No. WO 2008/019828 and inventors Steffen KAPPEL and Klaus BAUMGARTNER, are hereby incorporated by reference as if set forth in their entirety herein for the purpose of correcting and explaining any possible misinterpretations of the English translation thereof. In addition, the published equivalents of the above corresponding foreign and international patent publication applications, and other equivalents or corresponding applications, if any, in corresponding cases in the Federal Republic of Germany and elsewhere, and the references and documents cited in any of the documents cited herein, such as the patents, patent applications and publications, are hereby incorporated by reference as if set forth in their entirety herein.

The purpose of incorporating the Foreign equivalent patent application PCT/EP2007/007188 and German Patent Application 10 2006 038 255.2 is solely for the purpose of providing a basis of correction of any wording in the pages of the present application, which may have been mistranslated or misinterpreted by the translator. Words relating to opinions and judgments of the author and not directly relating to the technical details of the description of the embodiments therein are not to be incorporated by reference. The words all, always, absolutely, consistently, preferably, guarantee, particularly, constantly, ensure, necessarily, immediately, endlessly, avoid, exactly, continually, expediently, need, must, only, perpetual, precise, perfect, require, requisite, simultaneous, total, unavoidable, and unnecessary, or words substantially equivalent to the above-mentioned word in this sentence, when not used to describe technical features of one or more embodiments, are not generally considered to be incorporated by reference herein.

Statements made in the original foreign patent applications PCT/EP2007/007188 and DE 10 2006 038 255.2 from which this patent application claims priority which do not have to do with the correction of the translation in this patent application are not to be included in this patent application in the incorporation by reference.

All of the references and documents, cited in any of the documents cited herein, are hereby incorporated by reference as if set forth in their entirety herein. All of the documents cited herein, referred to in the immediately preceding sentence, include all of the patents, patent applications and publications cited anywhere in the present application.

The description of the embodiment or embodiments is believed, at the time of the filing of this patent application, to adequately describe the embodiment or embodiments of this patent application. However, portions of the description of the embodiment or embodiments may not be completely applicable to the claims as originally filed in this patent application, as amended during prosecution of this patent application, and as ultimately allowed in any patent issuing from this patent application. Therefore, any statements made relating to the embodiment or embodiments are not intended to limit the claims in any manner and should not be interpreted as limiting the claims in any manner.

The details in the patents, patent applications and publications may be considered to be incorporable, at applicant's option, into the claims during prosecution as further limitations in the claims to patentably distinguish any amended claims from any applied prior art.

The purpose of the title of this patent application is generally to enable the Patent and Trademark Office and the public to determine quickly, from a cursory inspection, the nature of this patent application. The title is believed, at the time of the filing of this patent application, to adequately reflect the general nature of this patent application. However, the title may not be completely applicable to the technical field, the object or objects, the summary, the description of the embodiment or embodiments, and the claims as originally filed in this patent application, as amended during prosecution of this patent application, and as ultimately allowed in any patent issuing from this patent application. Therefore, the title is not intended to limit the claims in any manner and should not be interpreted as limiting the claims in any manner.

The abstract of the disclosure is submitted herewith as required by 37 C.F.R. §1.72(b). As stated in 37 C.F.R. §1.72(b):

A brief abstract of the technical disclosure in the specification must commence on a separate sheet, preferably following the claims, under the heading "Abstract of the Disclosure." The purpose of the abstract is to enable the Patent and Trademark Office and the public generally to determine quickly from a cursory inspection the nature and gist of the technical disclosure. The abstract shall not be used for interpreting the scope of the claims.

Therefore, any statements made relating to the abstract are not intended to limit the claims in any manner and should not be interpreted as limiting the claims in any manner.

The embodiments of the invention described herein above in the context of the preferred embodiments are not to be taken as limiting the embodiments of the invention to all of the provided details thereof, since modifications and variations thereof may be made without departing from the spirit and scope of the embodiments of the invention.

What is claimed is:

1. A container treatment arrangement comprising:
at least one sprayer configured to spray a treatment material into the interior of a container to clean and/or disinfect the interior surface of the container;
a deflector arrangement comprising a moving arrangement and a deflector;
said moving arrangement comprising a lever to which said deflector is fixed at least while a cleaning and/or disinfecting of the container is performed;
said lever being pivotable to move said deflector between an active position in which said deflector is positioned, in the place of the container and over said at least one sprayer, to deflect sprayed treatment material toward a portion of said container treatment arrangement, and an inactive position in which said deflector does not deflect sprayed treatment material;
at least one container handling structure configured to hold the container in an upright position, then move the container into an upside-down position over said at least one sprayer for cleaning and/or disinfecting, and then move the container back into an upright position; and
said deflector, upon being in said active position, is configured to deflect sprayed treatment material toward said at least one sprayer to clean and/or disinfect outer surfaces of said at least one sprayer, and to additionally deflect sprayed treatment material toward said at least one container handling structure to clean and/or disinfect outer surfaces of said at least one container handling structure.

2. The container treatment arrangement according to claim 1, wherein:
said lever is pivotable about an axis of rotation; and
said deflector arrangement comprises an actuator configured to adjust the vertical position of said deflector in the active position with respect to said at least one sprayer.

3. The container treatment arrangement according to claim 2, wherein said actuator comprises a pneumatic cylinder.

4. The container treatment arrangement according to claim 3, wherein said moving arrangement comprises a drive motor which defines the axis of rotation of said lever, or which is connected to said lever at the axis of rotation of said lever.

5. The container treatment arrangement according to claim 4, wherein said lever is a one-armed lever.

6. The container treatment arrangement according to claim 5, wherein:
said container treatment arrangement comprises a collecting basin configured to collect sprayed treatment material; and
said deflector has an elongated, curved shape and is configured to deflect sprayed treatment material toward said collecting basin.

7. The container treatment arrangement according to claim 6, wherein said lever is configured to move said deflector over an angular distance of approximately 180 degrees upon movement between said active position and said inactive position.

8. The container treatment arrangement according to claim 7, wherein said deflector has a substantially U-shaped cross-section and comprises a base portion and two side portions, which said two side portions face one another and extend from opposite ends of said base portion.

9. The container treatment arrangement according to claim 7, wherein:
said at least one sprayer comprises a spray tube;
said deflector has a substantially closed cross-section and comprises an enclosing wall arrangement; and
said wall arrangement comprises an opening therein configured to permit insertion of said spray tube into said deflector.

10. The container treatment arrangement according to claim 9, wherein said container treatment arrangement comprises a return line connected to said deflector to remove collected sprayed material from the interior of said deflector.

11. The container treatment arrangement according to claim 2, wherein:
said moving arrangement comprises a drive motor which defines the axis of rotation of said lever, or which is connected to said lever at the axis of rotation of said lever.

12. The container treatment arrangement according to claim 1, wherein said deflector arrangement comprises an actuator configured to adjust the vertical position of said deflector in the active position with respect to said at least one sprayer.

13. The container treatment arrangement according to claim 1, wherein:
said container treatment arrangement comprises a collecting basin configured to collect sprayed treatment material; and
said deflector has an elongated, curved shape and is configured to deflect sprayed treatment material toward said collecting basin.

14. The container treatment arrangement according to claim 1, wherein said deflector has a substantially U-shaped cross-section and comprises a base portion and two side portions, which said two side portions face one another and extend from opposite ends of said base portion.

15. The container treatment arrangement according to claim 1, wherein:
said at least one sprayer comprises a spray tube;
said deflector has a substantially closed cross-section and comprises an enclosing wall arrangement; and
said wall arrangement comprises an opening therein configured to permit insertion of said spray tube into said deflector.

16. The container treatment arrangement according to claim 15, wherein said container treatment arrangement comprises:
a return line connected to said deflector to remove collected sprayed material from the interior of said deflector; and
an adjustment mechanism configured to adjust the vertical position of said spray tube with respect to said deflector.

* * * * *